US007247458B2

(12) United States Patent
Bao et al.

(10) Patent No.: US 7,247,458 B2
(45) Date of Patent: Jul. 24, 2007

(54) ENZYMATIC DECARBOXYLATION OF 2-KETO-L-GULONIC ACID TO PRODUCE XYLOSE

(75) Inventors: Wuli Bao, Forsyth, IL (US); Leif P. Solheim, Decatur, IL (US); Steven F. Stoddard, Cerro Gordo, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 11/114,401

(22) Filed: Apr. 26, 2005

(65) Prior Publication Data

US 2005/0239174 A1 Oct. 27, 2005

Related U.S. Application Data

(60) Provisional application No. 60/565,640, filed on Apr. 27, 2004.

(51) Int. Cl.
  C12P 19/02 (2006.01)
  C12P 7/18 (2006.01)
  C12Q 1/68 (2006.01)
  C12N 9/24 (2006.01)
  C12N 1/19 (2006.01)
  C12N 15/70 (2006.01)
  C12N 15/74 (2006.01)

(52) U.S. Cl. .................. 435/105; 435/200; 435/471; 435/158; 435/6; 435/254.11; 435/320.1

(58) Field of Classification Search ............... 435/105, 435/158, 200, 252.3, 6, 254.1, 320.1, 471
See application file for complete search history.

(56) References Cited

FOREIGN PATENT DOCUMENTS

| WO | WO 98/17819 | 4/1998 |
| WO | WO 02/088154 A1 | 11/2002 |
| WO | WO 03/097848 | 11/2003 |

OTHER PUBLICATIONS

Chang et al. Effects of deletions at the carboxyl terminus of Zymomonas mobilis pyruvate decarboxylase on the kinetic properties and substrate specificity, Biochemistry. Aug. 8, 2000;39(31):9430-7.*
Sasajima, K., et al. "Oxidation of L-Glucose By a *Pseudomonad*," Biochimica et Biophysica Acta, 571 (1979), pp. 120-126.
Chotani, G., et al. "The Commercial Production of Chemicals Using Pathway Engineering," Biochimica et Biophysica Acta, 1543 (2000), pp. 434-455.
Saito, Y., et al. "Cloning of Genes Coding for L-Sorbose and L-Sorbosone Dehydrogenases from *Gluconobacter oxydans* and Microbial Production of 2-Keto-L-Gulonate, a Precursor of L-Ascorbic Acid, in a Recombinant *G. oxydans* Strain", Applied and Environmental Microbiology, Feb. 1997, pp. 454-460.
Raj, K., et al. "Cloning and Characterization of the *Zymobacter palmae* Pyruvate Decarboxylase Gene (*pdc*) and Comparison to Bacterial Homologues," Applied and Environmental Microbiology, Jun. 2002, pp. 2869-2876.
Horn, S., et al. "Production of Ethanol from Mannitol by *Zymobacter palmae*," Journal of Industrial Microbiology & Biotechnology, (2000) 24, pp. 51-57.
Nidetzky, B. et al. "Continuous Enzymatic Production of Xylitol with Simultaneous Coenzyme Regeneration in a Charged Membrane Reactor," Biotechnology and Bioengineering, vol. 52, pp. 387-396 (1996).
Liu, S., et al. "Functional Expression of Bacterial *Zymobacter palmae* Pyruvate Decarboxylase Gene in *Lactococcus lactis*," Current Microbiology, vol. 50 (2005), pp. 324-328.
Raj, Krishnan C. et al., "Cloning and characterization of the *Zymobacter palmae* pyruvate decarboxylase gene (*pdc*) and comparison to bacterial homologues," *Applied and Environmental Microbiology*, 2002, 2869-2876, (68)6.
Candy, JM et al., "Structure and Properties of pyruvate decarboxylase and site-directed mutagenesis of the *Zymomonas mobilis* enzyme," *Biochim Biophys Acta.*, 1998, 323-338, 1385(2).
Konig, S., "Subunit structure, function and organization of pyruvate decarboxylases from various organisms", *Biochim Biophys Acta.*, 1998, 271-86, 1385(2).
National Institutes of Health, National Center for Biotechnological Information, "*Acetobacter pasteurianus* putative aldehyde dehydrogenase (aldl) and pyruvate decarboxylase (pdc) genes, complete cds," Apr. 4, 2001, GENBANK, Accession No. AF368435.
National Institutes of Health, National Center for Biotechnological Information, "*Zymobacter palmae* pyruvate decarboxylase (pdc) gene, complete cds", Jan. 23, 2002, GENBANK, Accession No. AF474145.
National Institutes of Health, National Center for Biotechnological Information, *Aspergillus oryzae* pyruvate decarboxylase (pdcA) gene, complete cds, Oct. 13, 1998, GENBANK, Accession No. AF098293.
National Institutes of Health, National Center for Biotechnological Information, "*Arabidopsis thaliana* pyruvate decarboxylase, putative (At5g54960) mRNA, complete cds," Jul. 25, 2002, GENBANK, Accession No. NM_124878.
National Institutes of Health, National Center for Biotechnological Information, "*Arabidopsis thaliana* pyruvate decarboxylase, putative (At4g33070) mRNA, complete cds," Jul. 25, 2002, GENBANK, Accession No. NM_119461.
National Institutes of Health, National Center for Biotechnological Information, Gen Bank "*Saccharomyces kluyveri* CBS 3082 pyruvate decarboxylase (PDC11) gene, complete cds," May 19, 2003, GENBANK, Accession No. AY302469.
National Institutes of Health, National Center for Biotechnological Information, Gen Bank "*Candida glabrata* pyruvate decarboxylase (PDC) gene, complete cds," Sep. 9, 2002, GENBANK, Accession No. NM AF545432.

* cited by examiner

*Primary Examiner*—Rebecca E. Prouty
*Assistant Examiner*—Iqbal Chowdhury
(74) *Attorney, Agent, or Firm*—Kirkpatrick & Lockhart Preston Gates Ellis LLP

(57) ABSTRACT

The invention is drawn to the enzymatic decarboxylation of 2-keto-L-gulonic acid (2-KLG) to produce xylose. The invention is also drawn to a method to detect xylose in vitro or in vivo (intracellularly), which employs an L-xylose dehydrogenase.

6 Claims, No Drawings

ENZYMATIC DECARBOXYLATION OF 2-KETO-L-GULONIC ACID TO PRODUCE XYLOSE

This application claims the priority benefit of U.S. Provisional Application No. 60/565,640 which was filed on Apr. 27, 2004, and is incorporated by reference in its entirety.

BACKGROUND OF THE INVENTION

1. Field of the Invention

The present invention relates to a novel enzymatic method to produce xylose and a method of detecting xylose in vitro.

2. Background Art

Xylose is a pentose sugar. D-xylose is the form found primarily in plants and animals. Xylose is recognized as being useful as an additive; as a food; as a pre-cursor for xylitol; as a sweetener; as a glucose substitute for diabetic patients (xylose does not provoke insulin response like glucose); as a therapeutic for decreasing transaminase and ketone levels in hepatitis patients, for connective tissue disorders and for osteoarthritis; and for industrial uses, such as dyeing, tanning, furfural production, paint, acetic acid production, lactic acid production, biodegradeable plastic polymer production, glue, resins, vitamin C production, and ethanol fuel production.

Xylose is a major component of hemicellulose. Hemicellulose is a component of lignocellulose, which is found in plants, for example, forage plants, woody plants, bark, beechwood, corn husks, oat hulls, canes, coffee grounds, straw, and bulk plant products. Xylose can be recovered from agricultural waste and hardwood in good yield by acid hydrolysis, using acetic acid or sulfuric acid. However, acid hydrolysis of hemicellulose results in the presence of varying amounts of many hexoses and pentoses, including arabinose, galactose, mannose, rhamnose, and glucose, in the same preparation as the xylose.

Acid hydrolysis of lignocellulose, however, liberates different sugars, such as a mixture of D- and L-sugars, as well as furfurals, acetic acid, hydroxybenzoic acid and vanillin, among others. Therefore, processing xylose from bulk plant products or from sources of hemicellulose or lignocellulose suffers from the disadvantage of the presence of many products from the acid hydrolysis, making the extraction of xylose from the by-products costly. Some of these side products, in particular the furfurals, inhibit the growth of microorganisms. Therefore, one disadvantage of using sources of hemicellulose and lignocellulose for the production of xylose is that many of the products produced by acid hydrolysis of hemicellulose and lignocellulose inhibit microbial metabolism and subsequent utilization of the sugars (Ooi et al., *Electron. J Envrion. Agric. Food Chem.* 1(3), (2002)). Because of the numerous side products, additional purification of the xylose product is required.

Therefore, there exists a need for improved methods of producing xylose, which produces fewer by-products.

BRIEF SUMMARY OF THE INVENTION

An improved method is provided for preparing xylose in a cost-effective manner. The process involves enzymatic conversion of 2-KLG to xylose. A first aspect of the present invention is directed to a method of producing xylose. According to the method of the invention, L-xylose is produced by enzymatic decarboxylation of 2-keto-L-gulonic acid (2-KLG) with a pyruvate decarboxylase (PDC) that accepts 2-KLG as a substrate and that produces L-xylose as a product as a result of such decarboxylation. The 2-KLG that is the substrate of the reaction can be pure or part of a mixture, for example, a fermentation mixture. The L-xylose that is produced can be used directly or can be used to make other products, such as, for example, the commercially higher value product, xylitol, which can be manufactured by, for example, chemical reduction of xylose.

A second aspect of the present invention is directed to a method to detect xylose using an L-xylose dehydrogenase.

It is to be understood that both the foregoing general description and the following detailed description are exemplary and explanatory only and are intended to provide further explanation of the invention as claimed.

DETAILED DESCRIPTION OF THE INVENTION

Provided herein are methods for converting various substrates to xylose. In one aspect of the invention, 2-KLG is produced from precursor products such as glucose or sorbitol. In other aspects of the invention, PDC and recombinant forms of PDC are used to convert 2-KLG into xylose in microorganisms and in cell-free systems. Another aspect of the invention includes a method to detect xylose using L-xylose dehydrogenase. Xylose is useful in a variety of manufacturing, medical and agricultural applications.

Definitions

As used herein, the term "enzymatic decarboxylation" refers to the use of an enzyme to remove the carboxyl group from a molecule. For example, but not limited to, the use of a pyruvate decarboxylase to remove the carboxyl group from 2-KLG.

As used herein, the term "substrate" refers to the organic molecule upon which an enzyme acts. Particular substrates of the present invention include, but are not limited to, 2-KLG, glucose, sorbose, sorbitol, 2,5-DKG, gulonic acid, etc.

As used herein, the term "cofactor" refers to a molecule, such as a metallic ion or coenzyme, that must be associated with an enzyme for the enzyme to function. For example, but not limited to, magnesium ion, and thiamine pyrophospate.

As used herein, the term "heterologous protein" refers to a protein or polypeptide that does not occur naturally in the host in which it is expressed.

As used herein, the term "host cell" refers to any prokaryotic or eukaryotic cell in which a desired nucleic acid sequence has been introduced into the cell to accomplish a desired function. The metabolic processes and pathways of the host cell are typically capable of maintaining, replicating, and optionally expressing a foreign nucleic acid sequence, whether or not the sequence is inserted in the host cell's genome. There are a variety of suitable host cells, including, but not limited to, bacterial, fungal, and plant cells, that can be utilized in the present invention.

As used herein, the term "suitable media" means any media or substance capable of supporting and/or sustaining the growth of a host cell in culture.

As used herein, the term "gene" refers to a segment of DNA, RNA or sequence nucleic acids, which encodes and is capable of expressing a specific product. This product can be a protein or polypeptide or a structural or functional nucleic acid. In a broader sense, a gene can produce any desired product, whether the product is a protein, polypeptide or nucleic acid. Functional or structural nucleic acids, for example, rRNA, ribosomes, antisense RNA or interfering RNA (e.g., siRNA) may also be considered gene products.

A "gene" may also contain sequences containing regulatory elements, such as without limitation, promoters, enhancers and terminators, "operably linked" to the expressed sequence to facilitate the transcription of the expressed sequence. The expressed sequence can also contain introns.

As used herein, the term "pdc gene" means the nucleic acid sequence or gene encoding pyrovate decarboxylase or pdc (PDC) which can be derived from an organism which includes, but is not limited to, *Aspergillus*, such as *A. nidulans* and *A. oryzae* (e.g., GenBank Accession No. AF098293, SEQ ID NO: 3); plant cells such as maize, legumes, tobacco, *Arabidopsis* (e.g., *A. thaliana* PDC, GenBank Accession No. NM_124878, SEQ ID NO: 4; *A. thaliana* PDC-1, GenBank Accession No. NM_119461, SEQ ID NO: 5), rice, and wheat or wheat germ, among others; the bacteria, *Zymobacter* (e.g., GenBank Assession No. AF474145, SEQ ID NO: 2), and *Acetobacter* (e.g., GenBank Accession No. AF368435, SEQ ID NO: 1); yeasts, which include *Saccharomyces kluyveri* (e.g., Genbank Accession No. AY302469, SEQ. ID NO. 6; *Pichia* and *Zygosaccharomyces* and brewer's yeast; and fungal cells which include *Streptomyces, Candida glabrata* (e.g., GenBank Accession No. AF545432, SEQ ID NO: 7), and *Rhizopus*. In one embodiment, the pyruvate decarboxylase gene is derived from *Acetobacter pasteurianus* (SEQ ID NO: 1) or, in some other embodiments, *Zymobacter palmae* (SEQ ID NO: 2).

As used herein, the term "vector" is used in reference to nucleic acid molecules that transfer genetic material, such as DNA, from one cell to another. Retroviral vectors transfer RNA, which is then reverse transcribed into DNA. It is not intended, however, that the present invention be limited to retroviral or any other specific vector.

As used herein, the term "expression vector" refers to a recombinant molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The terms "promoter element" and "promoter" as used herein, refer to a DNA sequence that precedes a gene in a DNA polymer and provides a site for initiation of the transcription of the gene into mRNA.

As used herein, the term "selectable marker" refers to the use of a gene which encodes an enzymatic activity that confers resistance to an antibiotic or drug upon the cell in which the selectable marker is expressed. Selectable markers may be "dominant;" a dominant selectable marker encodes an enzymatic activity, which can be detected in any eukaryotic cell line. Examples of dominant selectable markers include the bacterial aminoglycoside 3' phosphotransferase gene (also referred to as the neo gene), which confers resistance to the drug G418 in mammalian cells; the bacterial hygromycin G phosphotransferase (hyg) gene, which confers resistance to the antibiotic hygromycin; and the bacterial xanthine-guanine phosphoribosyl transferase gene (also referred to as the gpt gene), which confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk7 cell lines, the CAD gene that is used in conjunction with CAD-deficient cells, and the mammalian hypoxanthine-guanine phosphoribosyl transferase (hprt) gene that is used in conjunction with hprf cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "polynucleotide sequence" or "nucleotide sequence" means any sequence of nucleotide units. The polynucleotide sequence can be a sequence of deoxyribonucleotides (abbreviated adenosine (A), guanosine (G), cytidine (C), and thymidine (T)). Alternatively, the polynucleotide can be a sequence of ribonucleotides, which would include the bases adenosine, guanosine, cytidine and uridine (U), where each thymidine in the specified deoxyribonucleotide sequence is replaced by the ribonucleotide uridine.

As used herein, the terms "complementary" or "complementarity" are used in reference to polynucleotides related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection in methods, which depend upon binding between nucleic acids.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the Tm of nucleic acids is well known in the art. As indicated by standard references, a simple estimate of the $T_m$ value may be calculated by the equation: $T_m = 81.5°$ C.$+0.41$(% G+C), when a nucleic acid is in aqueous solution at 1 M NaCl (See e.g., Anderson and Young, Quantitative Filter Hybridization, in Nucleic Acid Hybridization (1985)). Other references include more sophisticated computations, which take structural as well as sequence characteristics into account for the calculation of $T_m$.

As used herein, the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

As used herein, the term "amplifiable nucleic acid" is used in reference to nucleic acids, which may be amplified by any amplification method. It is contemplated that an "amplifiable nucleic acid" will usually comprise a "sample template."

As used herein, the term "sample template" refers to a nucleic acid originating from a sample that is analyzed for the presence of a "target." In contrast, "background template" is used in reference to nucleic acid other than sample template, which may or may not be present in a sample. Background template is most often inadvertent. It may be the result of carryover, or it may be due to the presence of nucleic acid contaminants sought to be purified away from the sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a relatively short sequence of nucleotides), whether occurring naturally as in a purified restriction digest or produced synthetically, which is capable of hybridizing to another oligonucleotide of interest. Probes are useful in the detection, identification and isolation of particular gene sequences. It is contemplated that any probe used in the present invention will be labeled with a "reporter molecule," so that it is detectable in any detection system, including, but not limited to, enzyme (e.g., ELISA, as well as enzyme-based histochemical assays), fluorescent, radioactive, and luminescent systems. It is further contemplated that the oligonucleotide of interest (i.e., to be detected) will be labeled with a reporter molecule. It is also contemplated that both the probe and oligonucleotide of interest will be labeled. It is not intended that the present invention be limited to any particular detection system or label.

As used herein in reference to the polymerase chain reaction, the term "target" refers to the region of nucleic acid bounded by the primers used for polymerase chain reaction. Thus, the "target" is sought to be sorted out from other nucleic acid sequences. In other embodiments, the term refers to any nucleic acid (or region of nucleic acid) of interest. A "segment" is defined as a region of nucleic acid within the target sequence.

As used herein, the term "polymerase chain reaction" ("PCR") refers to the methods of U.S. Pat. Nos. 4,683,195, 4,683,202, and 4,965,188, all of which are hereby incorporated by reference, directed to methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., *Proc. Nat. Acad. Sci USA* 69:3038 (1972)). Other nucleic acid will not be replicated by this amplification enzyme. Similarly, in the case of T7 RNA polymerase, this amplification enzyme has a stringent specificity for its own promoters (Chamberlin et al., *Nature* 228:227 (1970)). In the case of T4 DNA ligase, the enzyme will not ligate the two oligonucleotides where there is a mismatch between the oligonucleotide substrate and the template at the ligation junction (Wu and Wallace, *Genomics* 4:560 (1989)). Finally, thermostable polymerases, such as Taq and Pfu, by virtue of their ability to function at high temperature, are found to display high specificity for the sequences bounded and, thus, defined by the primers; the high temperature results in thermodynamic conditions that favor primer hybridization with the target sequences and not hybridization with non-target sequences.

Some amplification techniques, such as PCR and nucleic acid sequence-based amplification (NASBA) take the approach of amplifying and then detecting target; others, such as rolling circle amplification (for example, with a padlock probe), detect target and then amplify the probe. Regardless of the approach, nucleic acid must be free of inhibitors for amplification to occur at high efficiency.

As used herein, the terms "PCR product," "amplicon" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "nested primers" refers to primers that anneal to the target sequence in an area that is inside the annealing boundaries used to start PCR (Mullis, et al., Cold Spring Harbor Symposia, Vol. 11, pp. 263-273 1986). Because the nested primers anneal to the target inside the annealing boundaries of the starting primers, the predominant PCR-amplified product of the starting primers is necessarily a longer sequence, than that defined by the annealing boundaries of the nested primers. The PCR-amplified product of the nested primers is an amplified segment of the target sequence that cannot, therefore, anneal with the starting primers. Advantages to the use of nested primers include the large degree of specificity, as well as the fact that a smaller sample portion may be used and yet obtain specific and efficient amplification.

As used herein, the term "amplification reagents" refers to those reagents (deoxyribonucleoside triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" typically refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. Enhancer elements, however, can exert their effect even when located 3' of the promoter element and the coding region. Transcription termination and polyadenylation signals are typically located 3' or downstream of the coding region.

As used herein, the term "a nucleotide sequence encoding a gene" means a DNA sequence comprising the coding region of a gene or in other words the DNA sequence that encodes a gene product. The coding region may be present in either a cDNA or genomic DNA form. Suitable control elements such as enhancers/promoters, splice junctions, polyadenylation signals, etc. may be placed in close proximity to the coding region of the gene if needed to permit proper initiation of transcription and/or correct processing of the primary RNA transcript.

Alternatively, the coding region utilized in the present invention may contain endogenous enhancers/promoters, splice junctions, intervening sequences, polyadenylation signals, etc. or a combination of both endogenous and exogenous control elements.

As used herein, the term "transcription unit" refers to the segment of DNA between the sites of initiation and termination of transcription and the regulatory elements necessary for the efficient initiation and termination. For example, a segment of DNA comprising an enhancer/promoter, a coding region and a termination and polyadenylation sequence comprises a transcription unit.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis et al., *Science* 236:1237 (1987)). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see Voss et al., *Trends Biochem. Sci.*, 11:287 (1986); and Maniatis et al., supra (1987)). For example, the SV40 early gene enhancer is very active in a wide variety of cell types from many mammalian species and has been widely used for the expression of proteins in mammalian cells (Dijkema et al., *EMBO J.*, 4:761 (1985)). Two other examples of promoter/enhancer elements active in a broad range of mammalian cell types are those from the human elongation factor 1α gene (Uetsuki et al., *J. Biol. Chem.*, 264:5791 (1989); Kim et al., *Gene* 91:217 (1990); and Mizushima and Nagata, *Nucl. Acids. Res.*, 18:5322 (1990)) and the long terminal repeats of the Rous sarcoma virus (Gorman et al., *Proc. Natl. Acad. Sci. USA* 79:6777 (1982)) and the human cytomegalovirus (Boshart et al., *Cell* 41:521 (1985)).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats (LTRs) of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques) such that transcription of that gene is directed by the linked enhancer/promoter.

The presence of "splicing signals" on an expression vector often results in higher levels of expression of the recombinant transcript. Splicing signals mediate the removal of introns from the primary RNA transcript and consist of a splice donor and acceptor site (See e.g., Sambrook. et al., Molecular Cloning: A Laboratory Manual, 2nd ed., Cold Spring Harbor Laboratory Press, New York (1989), pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length.

The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene. A commonly used heterologous poly A signal is the SV40 poly A signal. The SV40 poly A signal is contained on a 237 bp Bam HI/Bcl I restriction fragment and directs both termination and polyadenylation (Sambrook, supra, at 16.6-16.7).

Eukaryotic expression vectors may also contain "viral replicons" or "viral origins of replication." Viral replicons are viral DNA sequences which allow for the extrachromosomal replication of a vector in a host cell expressing the appropriate replication factors. Vectors which contain either the SV40 or polyoma virus origin of replication replicate to high copy number (up to $10^4$ copies/cell) in cells that express the appropriate viral antigen. Vectors which contain the replicons from bovine papillomavirus or Epstein-Barr virus replicate extrachromosomally at low copy number (~100 copies/cell).

The term "stable transfection" or "stably transfected" refers to the introduction and integration of foreign DNA into the genome of the transfected cell. The term "stable transfectant" refers to a cell that has stably integrated foreign DNA into the genomic DNA.

The terms "transient transfection" and "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA, but have failed to integrate this DNA.

As used herein, the terms "nucleic acid molecule encoding," "nucleotide sequence encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "adoptive transfer" is used in reference to the transfer of one function to another cell or organism.

As used herein, the term "chemically reduced" means to add protons to a molecule by stoicometrically balanced chemical reactions.

As used herein, the term "microbially reduced" means to add protons to a molecule through enzymatic reactions as found in a microorganism.

As used herein, the term "cell free system" refers to a system without use of live, whole cells. A "cell free system" can include, but is not limited to, the use of cell lysates, extracts of cells, or cell fragments.

As used herein, the term "cell lysate" refers to a composition of cells that have been lysed wherein the internal contents of the cells is no longer contained by a membrane.

A. Pyruvate Decarboxylase

Pyruvate decarboxylase (PDC) catalyses the conversion of pyruvate to acetaldehyde, a key step in ethanol fermentation. The enzyme is a tetramer with each monomer containing one molecule of the cofactor thiamine diphosphate (3-[(4-amino-2-methylpyrimidin-5-yl)methyl]-5-(2-diphospho-ethyl)-4-methyl-1,3-thiazolium), associated with a magnesium ion. Normally, the enzyme catalyzes the breakdown of pyruvate into acetaldehyde and carbon dioxide as follows:

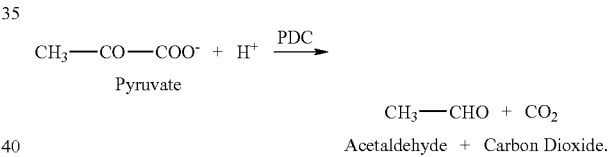

It has now been found that PDC will accept 2-KLG as a substrate, with the product being L-xylose.

The structure of 2-KLG and xylose are shown below.

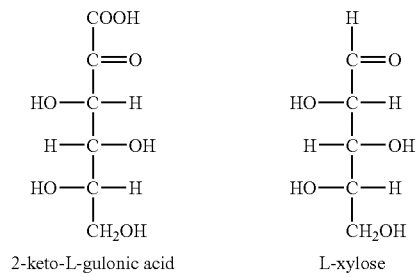

According to the invention, this property is used to produce L-xylose from 2-KLG.

As well-characterized herein, PDC that is useful in the methods of the invention may be purified or isolated from any desired source. For example, a PDC useful in the methods of the invention can be extracted, or even isolated from, a bacteria, plant, yeast, or fungi. Examples of PDC useful in the methods of the invention are the bacterial PDC described by Candy and Duggleby (*Biochim. Biophys. Acta*, 1385:323-338 (1998), and König (*Biochim Biophys. Acta*, 1385:271-286 (1998). Additional examples of nucleotide and amino acid sequences for certain PDC homologs are from *Acetobacter pasteurians* (GenBank Accession No. AF368435, SEQ ID NO: 1), and *Zymobacter palmae* (GenBank Accession No. AF474145, SEQ ID NO: 2).

The PDC in vitro reactions may be in soluble form, immobilized or otherwise contained within a structure such as a semi-permeable membrane that facilitates the removal of the enzyme from the L-xylose product. PDC can also be removed from the reaction mixture by precipitation with any of a variety of agents used to precipitate proteins, for example, ammonium sulfate acetone, trichloric acetic acid or other methods known to those skilled in the art.

B. Cell Free Systems

The method of the invention can be performed in vitro in cell free systems, or in a system wherein one or more of the necessary enzymes are produced by or provided by other organisms, and especially, microorganisms. An embodiment includes the use of crude extracts of microorganisms or cell lysates containing the enzymes and cofactors required for the production of xylose. In a cell free system, the PDC and/or the 2-KLG can be added in a purified form, along with other necessary reaction substrates and cofactors, in an assay medium with suitable buffers that facilitate or permit the enzymatic activity.

In a particular embodiment, xylose can be produced by providing PDC in a cell-free or purified form with other necessary reaction substrates and cofactors, in an assay medium at a pH that facilitates or permits the enzymatic activity. Either concurrently or consecutively, 2-KLG would be introduced into the assay medium containing pyruvate decarboxylase, wherein the 2-KLG is decarboxylated by the pyruvate decarboxylase to produce xylose. The xylose would then be purified. Any PDC can be used as the source of the PDC enzymatic activity as long as the PDC accepts 2-KLG as a substrate. The ability for PDC to accept 2-KLG as a substrate can be determined by methods known to those skilled in the art.

In a particular embodiment, including an in vitro cell free system, the 2-KLG is added in a purified form, along with other necessary reaction substrates and cofactors, in an assay medium with buffers and a pH that facilitates or permits the enzymatic activity. The assay is performed for a time, typically sufficient to either exhaust the 2-KLG substrate or to produce sufficient L-xylose so as to allow for the recovery of the same.

1. Lysate

In some embodiments, the enzymes, such as, but not limited to, PDC and 2-KDG reductase, can be in the form of a lysate. The lysate can be partially purified, substantially purified, or contained in the microorganisms of the invention. The lysate can be in any form allowing the enzymes to perform their intended function such as producing a desired product, such as PDC for catalyzing 2-KLG's conversion to xylose. The microorganisms can be whole permeabilized cells, membranes, or other portions of the cells necessary to obtain the desired end result. The microorganisms can be suspended in an appropriate solution such as buffered solutions or media, be rinsed free of media, or be freeze-dried or chemically dried, using known reagents such as acetone. The microorganisms can be immobilized with in a hydrogel, such as without limitation, polyvinylpyrrollidone hydrogel, polyacrylamide gel, chromatography medium or on synthetic supports, for example, multiple well plates, beads, matrices and the like so long as the supports support the cells in their intended use. The microorganisms can be fixed, cross-linked, or having permeabilized membranes with or without cell walls such that substrates, intermediates or products can more easily pass through said membrane with or without cell wall.

C. 2-Keto-L-Gulonic Acid (2-KLG)

The 2-KLG can be provided in a pure form or it can be generated in the cell as a product of cellular metabolism or other cellular processes. The 2-KLG can be commercially purchased, or synthetically produced, especially on an industrial scale. For example, one way to produce 2-KLG uses the Reichstein method (Reichstein and Grussner, *Helvetica Chimica Acta* 17:311 (1934) and Chotani, G. et al, *Biochim. Biophys. ACTA* 1543:434-455 (2000)) in which D-glucose is hydrogenated to form D-sorbitol, which is fermented into L-sorbose. The L-sorbose is converted diacetone-L-sorbose by acetonization. The diacetone-L-sorbose is then converted to 2-KLG by oxidation and hydrolysis.

1. In Vivo 2-KLG Production

One or more of the reactions for the production of 2-KLG can also be performed in vivo, that is, in living cells. The appropriate substrates can be provided to the cells as long as the cells' membranes are permeable to the substrate. See U.S. Pat. No. 5,989,891 for examples, herein incorporated by reference.

a. 2-KLG Production Using Glucose as a Substrate

In another embodiment, the 2-KLG is synthesized from D-glucose as a within a cell according to the following.

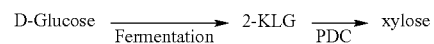

The production of 2-KLG from D-glucose is reviewed in Chotani et al., *Biochim. Biophys. Acta*, 1543:434-455 (2000) and described in more detail supra. Briefly, 2-KLG can be produced by the synthesis of 2,5-diketo-D-gluconic acid (2,5-DKG) from D-glucose using a microorganism, followed by a reduction of 2,5-DKG to 2-KLG, see supra. Illustrative examples are included in: EP 046 284; U.S. Pat. No. 5,998,634; U.S. Pat. No. 3,963,574; Sonoyama et al., *Agric. Biol. Chem.* 51:3039-3047 (1987); and Chotani et al., *Biochim. Biophys. Acta*, 1543:434-455 (2000). The microorganism host cell used in this embodiment may be genetically engineered to produce an enzyme involved in the processing of 2,5-DKG, such as 2,5-DKG reductase. The host cell strain would then be able to synthesize 2,5-DKG from D-glucose and endogenously reduce the 2,5-DKG with 2,5-DKG reductase to produce 2-KLG in the same cell. Illustrative examples are included in Anderson et al., *Science* 230:144-149, (1985); Chotani et al., (2000); Stewart, D. J. *Nature* 183:1133-1134, (1959); EP 132 308; U.S. Pat. Nos. 5,998,634; 4,757,012; 4,758,514; 5,004,690; 5,008,193; 5,032,514; WO 98/59054 and WO 00/37667 and Japanese Patent Publication Nos. 39-14493, 53-25033, 56-15877, and 59-35290.

Similar processes involving the microbial oxidation of D-glucose to 2,5-DKG followed by microbial or chemical reduction to 2-KLG can also be performed. For example, in a particular embodiment, glucose can be enzymatically or non-enzymatically oxidized to gluconic acid, then converted to 2-KDG, which is then ultimately reduced to 2-KLG.

b. KLG Production Using Sorbose or Sorbitol as a Substrate

In yet another embodiment, 2-KLG can be produced using bacterial strains that ferment L-sorbose and/or D-sorbitol to 2-KLG. Illustrative examples are disclosed in Saito et al., *Appl. Envrion. Microbiol.* 63:454-460, (1997); Shinjoh et al., *J. Bacteriol.* 184:861-863, (2002); and Chotani et al., (2000); and U.S. Pat. Nos. 6,541,239 B1, 6,319,699 B1, 5,989,891, and 5,834,231.

U.S. Pat. Nos. 6,541,239 B1, 6,319,699 B1 and 5,989,891 disclose processes for the production of 2-KLG that comprise contacting a microorganism with L-sorbose for a sufficient time and then isolating the accumulated 2-KLG. The fermentation process typically involves cultivating a microorganism in a synthetic or natural culture medium containing L-sorbose for a sufficient time and then isolating the accumulated 2-KLG from the culture medium and/or cells of the microorganism.

Genetic engineering methods can be used develop hosts, such as bacteria, yeast, fungi, plants or animals, to produce 2-KLG. For example, genetic engineering can be used to engineer such hosts to produce 2-KLG from substrates that may otherwise not be converted into 2-KLG or a 2-KLG precursor, such as L-sorbose (Saito et al., *Appl. Envrion. Microbiol.* 63:454-460 (1997)), or to make 2-KLG from D-glucose.

In one embodiment, without limitation, bacterial strain NRRL B-21627 (ADM X6L, *Ketogulonigenium robustum*) or a mutant or variant thereof, which is capable of producing at least about 40 g/L of 2-KLG from L-sorbose by fermentation in pure culture is used to produce 2-KLG. See U.S. Pat. No. 6,541,239. Strain ADM X6L was deposited at the Agricultural Research Service Culture Collection (NRRL), 1815 North University Street, Peoria, Ill. 61604, USA, on Oct. 1, 1996, under the provisions of the Budapest Treaty and assigned accession number NRRL B-21627.

In addition to naturally occurring strain NRRL B-21627 (ADM X6L), mutants and variants thereof may also be employed in the method of the invention. In particular embodiments, these mutants and variants are capable of producing at least 40 g/L of 2-KLG from L-sorbose in monoculture. See U.S. Pat. No. 6,541,239, herein incorporated by reference.

In yet another embodiment, mutant (ADM 86-96) of strain NRRL B-21627 (ADM X6L) was deposited at the Agricultural Research Service Culture Collection (NRRL), 1815 North University Street, Peoria, Ill. 61604, USA, on Oct. 15, 1996, under the provisions of the Budapest Treaty and assigned accession number NRRL B-21630. See U.S. Pat. No. 6,541,239, which provides examples of useful bacterial strains for production of 2-KLG for L-sorbose in culture.

In accordance with the present invention, the microorganism strain or a mutant or variant thereof that is used to produce the 2-KLG is contacted with L-sorbose for a sufficient time. The accumulated 2-KLG is isolated and decarboxylated for the production of xylose. In a particular embodiment, the microorganism strain is cultivated in a natural or synthetic medium containing L-sorbose for a period of time for 2-KLG to be produced, and the accumulated 2-KLG is subsequently isolated. Alternatively, a preparation derived from the cells of the microorganism strain, such as a lysate, is contacted with L-sorbose for a sufficient time and the accumulated 2-KLG is then isolated by conventional means.

In certain embodiments, the starting material, L-sorbose, is present in the medium prior to introduction of the microorganism strain or added to the medium after introduction of the strain, either all at once at the beginning or continuously or in installments over the course of cultivation. Alternatively, the L-sorbose is generated in situ by fermentative conversion of D-sorbitol. The amount of L-sorbose employed can be determined empirically by one skilled in the art, but is at least sufficient for the microorganism strain to produce at least about 40 g/L of 2-KLG. In an embodiment, L-sorbose comprises from 3 to 30% (w/v) of the culture medium, more preferably from 5 to 20%. In addition to L-sorbose and/or D-sorbitol, the natural or synthetic culture medium also contains a nitrogen source, suitable inorganic salts, and, as appropriate, various trace nutrients, growth factors and the like suitable for cultivation of the microorganism strain, and may also contain at least one supplementary carbon source. The amount of each of these additional ingredients to be employed is preferably selected to maximize 2-KLG production. In a particular embodiment of the present invention, the culture medium contains about 10% (w/v) of L-sorbose, about 3% (wt. dry solids/v) of corn steep liquor, and about 0.2% (w/v) of $MgSO_4.7H_2O$, with pH controlled using $NH_4OH$, $Ca(OH)_2$ or $CaCO_3$.

In another embodiment of the present invention, strain NRRL B-21627 (ADM X6L) or a mutant or variant thereof, such as NRRL B-21630 (ADM 86-96), is cultivated at a temperature in the range of 22° C. to 35° C., preferably about 30° C., and at a pH in the range of 5.0 to 8.0, preferably in the range of 5.5 to 7.5, more preferably about 6.0 to 6.8. The culture conditions employed can, of course, be varied by known methods at different time points during cultivation, as appropriate, to maximize 2-KLG production.

3. 2-KLG Isolation and Purification

The 2-keto-L-gulonic acid produced by the methods disclosed herein, can be isolated from the culture medium and purified by standard means. The 2-KLG is preferably about 70% pure, more preferably about 80% pure, more preferably about 90% pure, more preferably about 95%, and most preferably about 100% pure. After cultivation for a sufficient period of time, for example, from 10 to 150 hours, the 2-KLG that has accumulated in the cells and/or culture broth is isolated according to any of the known methods to those skilled in the art. Any method that is suitable with the conditions employed for cultivation may be used; illustrative examples of suitable methods for recovering 2-KLG are described in U.S. Pat. Nos. 5,474,924; 5,312,741; 4,960,695; 4,935,359; 4,877,735; 4,933,289; 4,892,823; 3,043,749; 3,912,592; 3,907,639 and 3,234,105.

According to one such method, microorganisms producing 2-KLG, are first removed from the culture broth by known methods, such as centrifugation or filtration, and the resulting solution concentrated under a vacuum. Crystalline 2-KLG is then recovered by filtration and, if desired, purified by recrystallization. Similarly, 2-KLG can be recovered using such known methods as the use of ion-exchange resins, solvent extraction, precipitation, salting out and the like. See U.S. Pat. No. 5,989,891.

When 2-KLG is recovered as a free acid, it can be converted to a salt, as desired, with sodium, potassium, calcium, ammonium or similar cations using conventional methods. Alternatively, when 2-KLG is recovered as a salt, it can be converted to its free form or to a different salt using conventional methods. See U.S. Pat. No. 6,541,239.

D. Decarboxylation of 2-KLG with PDC to Form Xylose

The decarboxylation of 2-KLG is accomplished in a reaction mixture comprising pyruvate decarboxylase (PDC), thiamine pyrophosphate (TPP) and 2-KLG. The reaction mixture typically contains a buffer or buffering system to maintain the pH of the mixture within a suitable range for the production of xylose from 2-KLG. In various embodiments, the conversion of 2-KLG to xylose occurs at buffer pH range from about 5 to about 7, from about 6 to about 7, from about 6 to about 8, from about 7 to about 8, or from about 7 to about 9. In certain embodiments, preferred pH ranges include from about 5.5 to about 7.5 or from about 6.5 to about 7.5, with one preferred target pH of about 5.75.

In certain embodiments, L-xylose is produced by culturing a microorganism that produces 2-KLG from D-glucose or L-sorbose. The microorganism would be incubated in a suitable medium for a sufficient time whereby the accumulated 2-KLG could be extracted or isolated. The 2-KLG would then be added to an appropriate assay medium containing PDC under conditions in which the 2-KLG is decarboxylated by the PDC to produce L-xylose.

1. Recombinant PDC

PDC can be produced through recombinant technologies using a host cell comprising a gene encoding PDC. Methods of introducing genetic material into host cells are well known to the skilled artisan, such as those described in typical molecular biology laboratory manuals including J. Sambrook, E. F. Fritsch and T. Maniatis, *Molecular Cloning: A Laboratory Manual*, 2d ed., Cold Spring Harbor Laboratory Press, Cold Spring Harbor, N.Y. (1989). These methods include, but are not limited to: calcium phosphate transfection, DEAE-dextran mediated transfection, microinjection, lipid-or liposome-mediated transfection, electroporation or viral-mediated infection. One embodiment of the present invention provides a host cell comprising the vector of the present invention.

Pyruvate decarboxylase can be produced in a microorganism comprising a plasmid carrying a pyruvate decarboxylase gene. Host cells of the invention include, but are not limited to, *Gluconobacter, Rhizobium, Bradyrhizobium, Alcaligenes, Rhodobacter, Rhodococcus, Azospirillum, Rhodospirillum, Sphingomonas, Burkholderia, Desulfomonas, Geospirillum, Succinomonas, Aeromonas, Shewanella, Halochromatium, Citrobacter, Escherichia, Klebsiella, Zymobacter, Fibrobacter, Acidobacter, Bacteroides, Sphingobacterium, Actinomyces, Corynebacterium, Nocardia, Rhodococcus, Propionibacterium, Bifidobacterium, Bacillus, Geobacillus, Paenibacillus, Sulfobacillus, Clostridium, Anaerobacter, Eubacterium, Streptococcus, Lactobacillus, Leuconostoc, Enterococcus, Lactococcus, Thermobifida, Cellulomonas*, and *Acetobacter*. Representative yeast cells include, but are not limited to, *Saccharomyces Kluyveromyces, Pichia* and *Zygosaccharomyces*. Representative fungal cells include, but are not limited to, *Streptomyces, Candida, Rhizopus* and *Aspergillus*. Preferred host cells of the invention include, but are not limited to *Eschericha coli*, and species of *Erwinia, Klebsiella, Enterobacter, Bacillus, Lactobacillus*, and *Streptomyces*.

Any nucleic acid sequence encoding a PDC that can use 2-KLG as a substrate is considered useful in the methods described herein. U.S. published Application No. 2003/0087368 A1 ("the '368 application") is drawn to nucleic acid molecules derived from *Zymobacter palmae* (SEQ ID NO: 2) that encode pyruvate decarboxylase that would be useful in the invention and is incorporated herein by reference.

An embodiment of the invention includes an expression vector, for instance a plasmid carrying a pyruvate decarboxylase (pdc) gene. The vector also includes suitable regulatory sequences for expressing the pdc sequence in a host cell, including without limitation: a promoter, an enhancer, a transcription termination signal (for example a polyadenylation (poly A) signal) and/or operator sequences as are well known in the art. The polynucleotide sequence encoding PDC and any regulatory sequences are "operably linked." That is, they are positioned on the expression vector to act in relation to the pdc sequence in their intended manner. The vector also can contain its native expression control sequences and/or expression control sequences that include chromosomal-, and episomal-derived control sequences, e.g., vectors derived from bacterial exogenous plasmids, bacteriophage, and vectors derived from combinations thereof, such as cosmids and phagemids.

In one particular embodiment of the invention, a recombinant expression vector contains a transcriptional unit comprising the isolated or recombinant pdc DNA sequences operably linked to a transcriptional promoter and a polyadenylation sequence. The expression vector contains either the full-length or functional fragments of the pdc gene, along with all the necessary regulatory sequences, including enhancers, promoters, and upstream and downstream regulatory sequences, and any other sequences necessary for expression and/or replication of the pdc gene. Examples of expression vectors used in particular embodiments include Litmus 28i (New England Biolabs, Beverly, Mass.) and pTrc99 (Pharmacia, Piscataway, N.J.).

In one embodiment, the polynucleotide pdc inserts and the polynucleotide signal encoding the signal peptide are operably linked to an appropriate promoter, including, but not limited to, its native promoter or a host-derived promoter, such as the phage lambda $P_L$ promoter, the phage lambda $P_R$ promoter, the *E. coli* lac promoters, such as the lacI and lacZ promoters (Kalnins A. et al., *EMBO J.* 2:593-597 (1983)), trp and tac promoters, the T3 and T7 promoters, the trc promoter and the gpt promoter. In an alternative embodiment, the promoter can be a eukaryotic promoter, such as the essentially constituitive cyto-megalo virus (CMV) promoter. In another embodiment, the promoter can be an inducible promoter, which is able to regulate the amount and timing of protein expression. Examples of an inducible promoter include, but are not limited to, TetOn and TetOff. TetOn is activated in the presence of tetracycline. The amount of expression of the gene of interest that operably linked to the promoter is proportional to the amount of tetracycline. TetOff works in the inverse fashion, whereby the presence of tetracycline inactivates the promoter. Other suitable promoters are known to those skilled in the art.

The expression vector also contains sites for transcription initiation, termination and, in the transcribed region, a ribosome binding site for translation. The coding portion of the mature transcripts expressed by the vector can include a translation initiating codon at the beginning and a termination codon appropriately positioned at the end of the polypeptide to be translated.

The expression vector also contains an origin of replication or other sequence that facilitates replication of the expression vector. For example, the *E. coli* replication origin. Alternatively, the expression vector contains a replication origin that is functional in bacteria, including, but not limited to *Erwinia, Klebsiella, Enterobacter, Bacillus, Lactobacillus*, or *Streptococcus*.

The expression vector typically contains one or more selectable markers which permits identification of successful transfections. The selectable marker is typically an antibiotic resistance gene. Suitable selectable markers include amikacin, augmentin (amoxicillin plus clavulonic acid), ampicillin, cefazolin, cefoxitin, ceftazidime, ceftiofur, cephalothin, enrofloxacin, florfenicol, gentamicin, imipenem, kanamycin, penicillin, sarafloxicin, spectinomycin, streptomycin, tetracycline, ticarcillin, tilmicosin, or chloramphenicol resistance genes. Other suitable markers will be readily apparent to the skilled artisan.

In particular embodiments of the invention, a host cell can contain apdc gene. The pdc gene can be exosomal (not integrated into a chromosome) or integrated into a chromosome. Integration of the pdc gene-containing expression vector may be accomplished using any number of standard techniques in the art without limit, such as by recombination using a Cre/IoxP system, as are commercially available. The host cell may contain a native gene that is modified to increase production of the product of the pdc gene construct of the present invention. For example, a stronger promoter may replace the native promoter, which will increase production of the protein encoded by the construct. In another example, an exogenous regulatory sequence can be spliced in which overrides a native signal to not express the gene of interest, i.e. TKT gene activation. See also, Raj et al., Appl. Environ. Microbiol. 2002, 68:2869-2876.

In an alternative embodiment, a host cell can include a nucleic acid sequence encoding PDC that has improved decarboxylase activity and/or improved thermal stability. In another embodiment, the host cell can include a nucleic acid sequence encoding PDC that has a higher affinity or higher activity for converting substrate, such as, but not limited to, 2-KLG to xylose. In yet another embodiment, the host cell can include modification(s) to enhance PDC production. For example, increased PDC synthesis can be achieved by either enhancing the activity of enzymes involved in synthetic pathways for PDC and/or the eliminating or reducing the feedback inhibition of metabolic pathways that control PDC production.

In certain embodiments, the host cell of the invention can contain a translated PDC polypeptide. The translated polypeptide can be expressed in a modified form, such as a fusion protein, and include additional heterologous functional regions. For instance, a region of additional particularly charged amino acids can be added to the N-terminus of the polypeptide to improve stability and persistence in the host cell during purification or subsequent handling and storage. Also, peptide moieties, such as a poly histidine tag, can be added to the polypeptide to facilitate purification using techniques such as affinity chromatography.

PDC Purification and Isolation

PDC purifications can be performed using standard procedures known in the art and as described but U.S. patent application Ser. No. 2003/0087368. In one embodiment, an *E. coli* expression system is used. *E. coli* comprising a pdc gene can be harvested by centrifugation and cells lysed using procedures known in the art (see, for example, U.S. patent application Ser. No. 2003/0087368). The cell lysate can be treated to remove cell debris and applied to an ion exchange column chromatography medium, such as Q-SEPHAROSE or DEAE; hydrophobic interaction chromatography medium, such as phenyl SEPHAROSE, or butyl SEPHAROSE; gel filtration chromatography media such as SUPERDEX, SEPHACRYL, SUPEROSE, or ULTROGEL AcA, or other medium known in the art, or any combinations thereof.

Culture Media

Culturing of the microorganisms and host cells described herein is performed in a suitable culture media. The medium used herein may be solid or liquid, synthetic or natural, and contains sufficient nutrients for the cultivation of the inventive microorganism strain. In certain embodiments, the medium employed is a liquid medium, or a synthetic liquid medium. Cultivation of the inventive microorganism strain may be accomplished using any of the submerged fermentation techniques known to those skilled in the art, such as airlift, traditional sparged-agitated designs, or shaking culture. Subsequent to culturing the host cells in culture media, the desired polypeptide is separated from the culture media by known methods, as described herein.

The natural or synthetic culture medium typically used in the invention contains a nitrogen source, suitable inorganic salts, and, as appropriate, various trace nutrients, growth factors and the like, suitable for cultivation of the microorganism strain, and may also contain at least one supplementary carbon source. In particular embodiments, the amount of each of these additional ingredients is selected to maximize the target protein production. In one particular embodiment, a protein-free media is used in order to facilitate purification of the target protein, such as, but not limited to, M9 minimum salt media (Sigma, St. Louis, Mo.) plus glucose. The amounts of additional ingredients may be determined empirically by one skilled in the art according to the various methods and techniques known in the art. The medium may contain other components as appropriate, such as peptone or N-Z Amine, supplemental carbon sources and/or various vitamins.

Illustrative examples of suitable supplemental carbon sources include, but are not limited to: other carbohydrates, such as glucose, fructose, mannitol, starch or starch hydrolysate, cellulose hydrolysate and molasses; organic acids, such as acetic acid, propionic acid, lactic acid, formic acid, malic acid, citric acid, and fumaric acid; and alcohols, such as glycerol.

Illustrative examples of suitable nitrogen sources include, but are not limited to: ammonia, including ammonia gas and aqueous ammonia; ammonium salts of inorganic or organic acids, such as ammonium chloride, ammonium nitrate, ammonium phosphate, ammonium sulfate and ammonium acetate; urea; nitrate or nitrite salts, and other nitrogen-containing materials, including amino acids as either pure or crude preparations, meat extract, peptone, fish meal, fish hydrolysate, corn steep liquor, casein hydrolysate, soybean cake hydrolysate, yeast extract, dried yeast, ethanol-yeast distillate, soybean flour, cottonseed meal, and the like.

Illustrative examples of suitable inorganic salts include, but are not limited to: salts of potassium, calcium, sodium, magnesium, manganese, iron, cobalt, zinc, copper and other trace elements, and phosphoric acid.

Illustrative examples of appropriate trace nutrients, growth factors, and the like include, but are not limited to: coenzyme A, pantothenic acid, biotin, thiamine, riboflavin, flavine mononucleotide, flavine adenine dinucleotide, other vitamins, amino acids such as cysteine, sodium thiosulfate, p-aminobenzoic acid, niacinamide, and the like, either as pure or partially purified chemical compounds or as present in natural materials.

In certain embodiments, the culture conditions employed, including temperature, pH, aeration rate, agitation rate, culture duration, and the like, may be determined empirically by one of skill in the art to maximize protein production. The selection of specific culture conditions depends upon factors such as the particular inventive microorganism strain employed, medium composition and type, culture technique, and similar considerations. Subsequent to culturing the host cells in culture media, the desired pyruvate decarboxylase is separated from the culture media by known methods in particular embodiments. The translated protein encoded by any pdc gene described herein, can be recovered and purified by well-known methods including ammonium sulfate or ethanol precipitation, acid extraction, anion or cation exchange chromatography, phosphocellulose chromatography, hydrophobic interaction chromatography, affinity chromatography, immunoprecipitation, hydroxylapatite chromatography, lectin chromatography, preparative high pressure liquid chromatography or fast performance liquid chromatography (FPLC), or combinations thereof. See Raj et al., Appl. Environ. Microbiol. 2002, 68:2869-2876.

E. Conversion of Xylose to Xylitol

The invention further includes a method of chemically reducing the xylose produced by any of the methods of the invention into xylitol. Xylose is converted to xylitol by a hydrogenation process. The structure of xylose and xylitol are shown below.

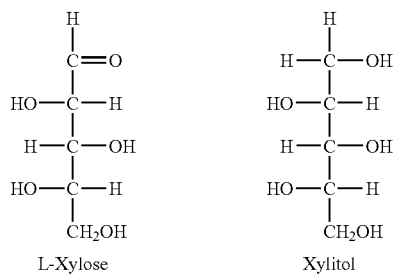

L-Xylose        Xylitol

In a particular embodiment, xylose is catalytically hydrogenated to xylitol in the presence of Raney nickel catalyst. This reaction typically occurs at high temperatures and pressure.

It is contemplated that that xylose can also be converted to xylitol by microbial means. In a particular embodiment, xylose is converted to xylitol in a microorganism by NADPH dependent xylose reductase. See Saha & Bothast, "Fuels and Chemicals from Biomass, Ch. 17, Microbial Production of Xylitol," pp. 307-319, 1997, herein incorporated by reference. An embodiment of the invention could include production of xylose from 2-KLG by PDC, wherein xylitol is converted from xylose by either chemical or microbial means.

F. Diagnostic Method to Measure Xylose Production

The invention further includes a method to measure the production of xylose comprising the detection of xylose using an L-xylose dehydrogenase (E.C. 1.1.1.113) derived from *Ochrobactrum anthropi*. See Sasjima and Sinskey, *Biochemica et Biophysica Acta*, 571:120-126 (1979).

L-xylose dehydrogenase is an oxidoreductase and catalyzes L-xylose to L-xylono-xylono-1,4-lactone (xylonic acid):

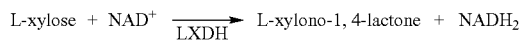

L-xylose dehydrogenase has been characterized in *Ochrobactrum anthropi* (Sasjima and Sinskey, *Biochemica et Biophysica Acta*, 571:120-126 (1979)). L-xylose dehydrogenase is also known as NADH-xylose reductase and L-xylose NAD 1-oxidoreductase. L-xylose dehydrogenase can also oxidize D-arabinose and L-glucose, although at slower rates than it oxidizes xylose.

When xylose is converted to xylonic acid, xylose is dehydrogenated and the hydride on H⁻ hydrogenates nicotinamide adenine dinucleotide (NAD) to form NADH. NADH production directly correlates with the amount of xylose dehydrogenated by L-xylose dehydrogenase. The formation of NADH can be monitored using a spectrophotometric method.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

EXAMPLES

Example 1

Cloning of the pdc gene from *Zymobacter palmae*. The pdc gene was cloned, sequenced, and expressed in *E. coli* (Raj et al., Appl. Environ. Microbiol. 2002, 68:2869-2876). Genomic DNA was prepared from *Zymobacter palmae* based on a method described by Harwood and Cutting (Molecular Biology Methods for *Bacillus*, Wiley Interscience, N.Y., 1990). PCR of the genomic DNA from *Zymobacter palmae* (ATCC 51623) resulted in the amplification and isolation of the DNA fragment that contains the open reading frame of the PDC enzyme. The primers were synthesized based on the sequence published in Raj et al., (Appl Environ. Microbiol. 2002, 68:2869-2876) with GenBank accession number AF474145. The PCR products containing the open reading frame of PDC was ligated into a vector plasmid, pTrc99 (Pharmacia Biotech Products, Piscataway, N.J.). The plasmid was transformed into *E. Coli* strain DH5α (Life Technologies, Rockville, Md.). The transformed *E. coli* was grown in Luria-Bertani (LB) medium and the expression of the gene was induced by addition of isopropyl-beta-D-thiogalactopyranoside (IPTG). The cells were harvested, washed by centrifugation, and then sonicated to produce an extract. The extract was assayed for PDC activity based on the method described by Raj et al, (Raj et al., Appl. Environ. Microbiol. 2002, 68:2869-2876).

Example 2

Decarboxylation of 2-KLG by PDC. A sample of *E. coli* PDC enzyme extract was provided. The *E. coli* overexpressed PDC enzyme derived from *Z. palmae*. PDC enzyme activity was determined by the method described by Raj et al. (Raj et al., Appl. Environ. Microbiol. 2002, 68:2869-2876).

Initial decarboxylation of 2-KLG was carried out using the enzyme extract. The reaction mixtures contained PDC derived from *Z. palmae* in a 50 mM citrate buffer, at pH 5.8, with 5 mM MgCl₂ (Sigma Biochemicals and Reagents, St. Louis, Mo.), 1 mM thiamine pyrophosphate (TPP) (Sigma Biochemicals and Reagents, St. Louis, Mo.) and 0.1% to 1% 2-KLG. The reaction mixtures were incubated at 50° C. for 15 hours. Xylose was produced in a dose dependent fashion ranging from 10 to 100 μg/ml. Xylose production directly correlated to the concentration of PDC used.

Example 3

Another experiment was performed using optimum conditions to confirm the production of xylose. The reaction mixtures contained 50 mM 2-morpholinoethanesulfonic acid (MES) (Sigma, St. Louis, Mo.), at a pH 5.75, with 5 mM $MgCl_2$, 1 M TPP, 300 mM 2-KLG, 0.1% ethanol, and PDC from bacterial extracts in the amounts listed in Table 1 below, to a total volume of 2.5 ml. Xylose was detected in the reaction mixtures ranging from 60-300 μg/ml using high pressure liquid chromatography (HPLC) and confirmed by gas chromatography after derivatization with trimethylsilane (TMS). A Carbopac PA20 (3×150 mm) column (Dionex, Sunnyvale, Calif.) was used in the HPLC analysis. Xylose was eluted from the column with 10 mM NaOH aqueous solution.

TABLE 1

| Reaction # | Protein (mg) | PDC (μg/min) | Source | Xylose (μg/ml) |
|---|---|---|---|---|
| 1 | 0.2 | 4 | PDC strain | 58.2 |
| 2 | 0.4 | 8 | PDC strain | 93.7 |
| 3 | 0.8 | 16 | PDC strain | 116.6 |
| 4 | 0.4 | 8 | PDC strain | 78.2 |
| 5 | 2.5 | 50 | PDC strain | 320 |
| 6* | 0.4 | 8 | PDC strain | ND |
| 7 | 2.0 | 0 | E. coli | ND |

*Reaction 6 contained no 2-KLG.
PDC strain was E. coli strain with plasmid containing PDC

Example 3

PCR mutagenesis of PDC open reading frame to improve its activity on 2-KLG. 2-KLG is not the natural substrate for PDC. The novel enzymatic reaction of the invention, 2-KLG decarboxylation by PDC, can be improved by further genetic engineering of the enzyme. DNA recombinant methods can be employed to modify the enzyme to have higher activity with 2-KLG.

In particular, the GeneMorph PCR Mutagenesis kit (#60050, Stratagene, La Jolla, Calif.) was used to generate mutuations with a PCR method. The plasmid of Example 1 was used as a template with the same primers for the mutagenesis PCR reactions. The PCR products were cloned into the plasmid pTrc99 (Pharmacia). Twenty clones were characterized for PDC activity and for their ability to decarboxylate 2-KLG. Compared to the control strain, which had no mutations, most of the 20 strains had less specific activity on native substrate, pyruvate, as well as on 2-KLG. This indicated that the mutations occurred in parts of the enzyme that are important for its activity.

Modifications in any of the enzymes or feedback regulatory components of the pathway of the invention leading to the production of xylose can also be made in order to further improve the activity or production of PDC. The production of xylose can also be made by genetic engineering methods or other metabolic manipulation methods.

Example 4

Diagnostic method to measure xylose production. L-xylose dehydrogenase activity was identified in the strain of Ochrobactrum anthropi (ATCC 29243, Manassas, Va.) by Sasajima and Sinskey (Biochimica et Biophysica Acta, 571:120-126). The methods of Sasajim and Sinskey are hereby incorporated by reference. These methods were performed in order to grow and make an extract from Ochrobactrum anthropi. L-xylose dehydrogenase was used to assay the amount of xylose produced in a given reaction by measuring NADH. When xylose is converted to xylonic acid, xylose is dehydrogenated and the hydride ion $H^-$ hydrogenates nictinamide adenine dinucleotide (NAD) to form NADH. NADH production directly correlates with the amount of xylose dehydrogenated by L-xylose dehydrogenase. The reaction contained 100 mM glycine buffer (Sigma, St. Louis, Mo.), at pH 10.0, with 2 mM NAD (Sigma), 0.01 mg protein of enzyme extract from O. anthropi and various amounts of xylose. The formation of NADH was monitored using a spectrophotometer to measure the increase of absorbance at 340 nm. This method can be altered by ones skilled in the art for use in assessing the activity of PDC's in a high throughput environment for PDC enzyme engineering.

Example 5

Conversion of xylose to xylitol. Reacting with good agitation, the reaction mixture would contain 40% to 45% xylose in an aqueous solution, at pH 5.0, 2% Raney Nickel catalyst. The reaction would be maintained at 1300 psig hydrogen pressure. The reaction would be started at a temperature of 60° C. and ramps to 140° C. over the course of 50 minutes. The reaction would be held at 140° C. and 1300 psig of pressure for approximately 45 minutes. The hydrogen gas would then be shut off and the reaction would be allowed to cool to about 85° C. in the span of approximately 30 minutes. Other methods, including, but not limited to, sodium borohydrate reduction can also be used to convert xylose to xylitol as known to those skilled in the art.

Example 6

Methods of producing xylose from 2-KLG derived glucose or sorbose. 2-KLG can be produced from sorbose in a microorganism as described in detail in U.S. Pat. Nos. 6,541,239 B1, 6,319,699 B1 and 5,989,891. Alternatively, 2-KLG can be produced from glucose as described in detail in EP 046 284; U.S. Pat. No. 5,998,634; U.S. Pat. No. 3,963,574; Sonoyama et al., Agric. Biol. Chem. 51:3039-3047 (1987); and Chotani et al., Biochim. Biophys. Acta, 1543:434-455 (2000). 2-KLG can be isolated by means known to those skilled in the art as discussed above. The isolated 2-KLG can then be used, as in Example 1, with PDC produced from a host cell. The 2-KLG can be contacted with the PDC to produce xylose. In another alternative, a microorganism can be engineered to express a PDC gene with increased ability to convert 2-KLG into xylose or xylitol, and would also have the ability to convert glucose or sorbose into 2-KLG. Therefore, the transformed organism could make L-xylose or xylitol directly from glucose or sorbose.

Having now fully described this invention, it will be understood to those of ordinary skill in the art that the same can be performed within a wide and equivalent range of conditions, formulations and other parameters without affecting the scope of the invention or any embodiment thereof. All patents and publications cited herein are fully incorporated by reference in their entirety.

We claim:

1. A method of producing L-xylose comprising enzymatically decarboxylating 2-keto-L-gulonic (2-KLG) acid to L-xylose, wherein the 2-KLG is decarboxylated using pyruvate decarboxylase obtained from *Zymobacter palmae*.

2. The method of claim 1, wherein the pyruvate decarboxylase is prepared from a host cell comprising a nucleic acid sequence encoding pyruvate decarboxylase operably linked to a promoter and a transcription termination sequence, and wherein the pyruvate decarboxylase nucleic acid sequence is from *Zyrmobacter palmae*.

3. The method of claim 1, wherein enzymatically decarboxylating the 2-keto-L-gulonic acid to the L-xylose comprises:

placing the 2-keto-L-gulonic acid in contact with pyruvate decarboxylase; and purifying the L-xylose.

4. The method of claim 3, further comprising admixing a buffer with the 2-keto-L-gulonic acid and the pyruvate decarboxylase to maintain a pH from about 5 to about 8.

5. A method of producing xylitol comprising enzymatically decarboxylating 2-keto-L-gulonic acid as set forth in the method of claim 3 and reducing the L-xylose produced to xylitol.

6. The method of claim 3, further comprising:

immobilizing the pyruvate decarboxylase.

* * * * *

SEQUENCE LISTING

<160> NUMBER OF SEQ ID NOS: 7

<210> SEQ ID NO 1
<211> LENGTH: 1674
<212> TYPE: DNA
<213> ORGANISM: Acetobacter pasteurianus

<400> SEQUENCE: 1

```
atgacctata ctgttggcat gtatcttgca gaacgccttg tacagatcgg gctgaagcat       60
cacttcgccg tgggcggcga ctacaatctc gttcttctgg atcagttgct cctcaacaag      120
gacatgaaac agatctattg ctgcaatgag ttgaactgtg gcttcagcgc ggaaggctac      180
gcccgttcta acgggctgc ggcagcggtt gtcaccttca gcgttggcgc catttccgcc       240
atgaacgccc tcggcggcgc ctatgccgaa aacctgccgg ttatcctgat tccggcgcg       300
cccaacagca atgatcaggg cacaggtcat atcctgcatc acacaatcgg caagacggat      360
tacagctacc agcttgaaat ggcccgtcag gtcacctgtg ccgccgaaag cattaccgac      420
gctcactccg ccccggccaa gattgaccac gtcattcgca cggcgctgcg cgagcgtaag      480
ccggcctatc tggacatcgc gtgcaacatt gcctccgagc cctgcgtgcg gcctggccct      540
gtcagcagcc tgctgtccga gcctgaaatc gaccacacga gcctgaaggc cgcagtggac      600
gccacggttg ccttgctgaa aaatcggcca gccccgtca tgctgctggg cagcaagctg       660
cgggccgcca acgcactggc cgcaaccgaa acgctggcag acaagctgca atgcgcggtg      720
accatcatgg cggccgcgaa aggcttttc cccgaagacc acgcgggttt ccgcggcctg       780
tactggggcg aagtctcgaa ccccggcgtg caggaactgg tggagacctc cgacgcactg      840
ctgtgcatcg cccccgtatt caacgactat tcaacagtcg gctggtcggg catgcccaag      900
ggccccaatg tgattctggc tgagcccgac cgcgtaacgg tcgatggccg cgcctatgac      960
ggctttaccc tgcgcgcctt cctgcaggct ctggcggaaa agcccccgc gcgcccggcc      1020
tccgcacaga aaagcagcgt cccgacgtgc tcgctcaccg cgacatccga tgaagccggt     1080
ctgacgaatg acgaaatcgt ccgtcatatc aacgccctgc tgacatcaaa cacgacgctg     1140
gtggcagaaa ccggcgattc atggttcaat gccatgcgca tgaccctggc cggtgcgcgc     1200
gtggaactgg aaatgcagtg gggccatatc ggctggtccg tgccctccgc gttcggcaat     1260
gccatgggct cgcaggaccg ccagcatgtg gtgatggtag cgatggctc cttccagctt     1320
accgcgcagg aagtggctca gatggtgcgc tacgaactgc ccgtcattat ctttctgatc     1380
aacaaccgtg gctatgtcat tgaaatcgcc attcatgacg gcccgtacaa ctatatcaag     1440
aactgggatt acgccggcct gatggaagtc ttcaacgccg gagaaggcca tggacttggc     1500
ctgaaagcca ccaccccgaa ggaactgaca gaagccatcg ccagggcaaa agccaatacc     1560
cgcggcccga cgctgatcga atgccagatc gaccgcacgg actgcacgga tatgctggtt     1620
caatggggcc gcaaggttgc ctcaaccaac gcgcgcaaga ccactctggc ctga           1674
```

<210> SEQ ID NO 2
<211> LENGTH: 1671
<212> TYPE: DNA
<213> ORGANISM: Zymobacter palmae

<400> SEQUENCE: 2

```
atgtataccg ttggtatgta cttggcagaa cgcctagccc agatcggcct gaaacaccac       60
tttgccgtgg ccggtgacta caacctggtg ttgcttgatc agctcctgct gaacaaagac      120
```

```
atggagcagg tctactgctg taacgaactt aactgcggct ttagcgccga aggttacgct     180
cgtgcacgtg gtgccgccgc tgccatcgtc acgttcagcg taggtgctat ctctgcaatg     240
aacgccatcg gtggcgccta tgcagaaaac ctgccggtca tcctgatctc tggctcaccg     300
aacaccaatg actacggcac aggccacatc ctgcaccaca ccattggtac tactgactat     360
aactatcagc tggaaatggt aaaacacgtt acctgcgcac gtgaaagcat cgtttctgcc     420
gaagaagcac cggcaaaaat cgaccacgtc atccgtacgg ctctacgtga acgcaaaccg     480
gcttatctgg aaatcgcatg caacgtcgct ggcgctgaat gtgttcgtcc gggcccgatc     540
aatagcctgc tgcgtgaact cgaagttgac cagaccagtg tcactgccgc tgtagatgcc     600
gccgtagaat ggctgcagga ccgccagaac gtcgtcatgc tggtcggtag caaactgcgt     660
gccgctgccg ctgaaaaaca ggctgttgcc ctagcggacc gcctgggctg cgctgtcacg     720
atcatggctg ccgaaaaagg cttcttcccg gaagatcatc cgaacttccg cggcctgtac     780
tggggtgaag tcagctccga aggtgcacag gaactggttg aaaacgccga tgccatcctg     840
tgtctggcac cggtattcaa cgactatgct accgttggct ggaactcctg ccgaaaggc      900
gacaatgtca tggtcatgga caccgaccgc gtcactttcg caggacagtc cttcgaaggt     960
ctgtcattga gcaccttcgc cgcagcactg gctgagaaag caccttctcg cccggcaacg    1020
actcaaggca ctcaagcacc ggtactgggt attgaggccg cagagcccaa tgcaccgctg    1080
accaatgacg aaatgacgcg tcagatccag tcgctgatca cttccgacac tactctgaca    1140
gcagaaacag gtgactcttg gttcaacgct ctcgcatgc cgattcctgg cggtgctcgt     1200
gtcgaactgg aaatgcaatg gggtcatatc ggttggtccg taccttctgc attcggtaac    1260
gccgttggtt ctccggagcg tcgccacatc atgatggtcg gtgatggctc tttccagctg    1320
actgctcaag aagttgctca gatgatccgc tatgaaatcc cggtcatcat cttcctgatc    1380
aacaaccgcg gttacgtcat cgaaatcgct atccatgacg gcccttacaa ctacatcaaa    1440
aactggaact acgctggcct gatcgacgtc ttcaatgacg aagatggtca tggcctgggt    1500
ctgaaagctt ctactggtgc agaactagaa ggcgctatca agaaagcact cgacaatcgt    1560
cgcggtccga cgctgatcga atgtaacatc gctcaggacg actgcactga aaccctgatt    1620
gcttggggta acgtgtagc agctaccaac tctcgcaaac cacaagcgta a              1671
```

<210> SEQ ID NO 3
<211> LENGTH: 1632
<212> TYPE: DNA
<213> ORGANISM: Aspergillus oryzae

<400> SEQUENCE: 3

```
atgtcgctga gtacctcttc aggcgacttc gtgaggttgg cgttcgtgca gtacacggtg      60
ttcctggtaa gcatcaatgc gccagcttgg gactacaact tggtggcttt ggattacctg     120
ccaaaatgcg atcttcattg ggtaggaaac tgtaatgagc ttaatgccgg atacgctgct     180
gatggatacg ctcgaatcaa tggaatgtct gctttagtca ccaccttttgg tgtgggtgag    240
ctatcggcgc tcaatgctat tgctggtgca tactccgaat ttgtgcctat cgttcacatt     300
gttggtcaac cgcatacgaa atcacagaaa gatggaatgc tcctccacca cacccttggc     360
aacggcgact tcaacgtctt caccagaatg agtgccgaca tctcttgcac acttggatgt     420
ttgaactcaa ctcacgaagt ggcgacccct cattgataatg ctatccgaga atgttggatt    480
cgtagtcgac cggtttatat ctctctccct accgatatgg tgacaaagaa aatcgaggga    540
```

```
gaacggctgg ataccctct cgatcttagt ctaccaccga acgatcccga aaaagaagat      600
tacgttgtgg atgtggttct caagtatctg cacgctgcaa agaaaccgt tattcttgtc       660
gatgcttgtg ctatccgcca tcgtgtgctc gatgaagttc atgagttcgt ggaaaaatct      720
gggctaccca cattcgtggc tccaatgggt aaaggagcag tggatgagac tcacaagaac      780
tacgcggtg tttacgctgg tactggatca aacccaggtg ttcgtgagca agtcgaatct       840
tcagacttga ttctgagcat cggtgctatc aagtccgatt tcaacacgac tgggttctct      900
taccgtattg ccaactcaa caccattgac ttccatagta catacgtgcg cgtccggtac       960
tccgaatacc ctgatatcaa catgaaaggc gtccttcaaa agattgttca agaatgggc      1020
aatctcaatg tcggaccagt ctcgccgccg tcgaacctac tgccggacaa cgagaaggca     1080
tcaaccgaac aggcgattac ccacgcatgg ctctggccta ctgtcgggca gtggctgaaa     1140
gaaaaggatg ttgttatcac ggaaaccggc actgccaatt tcggtatctg ggacactcgg     1200
ttcccggcag tgttacagc cattagtcag gttctttggg gtagtatcgg ctattcagtt      1260
ggagcttgtc aaggtgctgc gttggccgca aaagagcagg gccgacggac tgtactttc     1320
gtgggtgacg gaagtttcca gctgacgctc caggaagtca gcaccatgat aagaaataac     1380
cttaacccta tcatctttgt catttgcaac gaaggatata ccatcgaacg gtacattcat     1440
ggatgggaag ctgtttacaa tgacatccag ccctgggact tcttgaacat tcctgtggca    1500
tcggcgcga aggacaagta caaggatac aaggtcacaa cccgagacga gttgagggag      1560
cttttcgcaa atgaagaatt tgcttcggca ccctgtctcc agtttgaaat tgacagccga     1620
atcggccgct ga                                                          1632

<210> SEQ ID NO 4
<211> LENGTH: 1824
<212> TYPE: DNA
<213> ORGANISM: Arabidopsis thaliana

<400> SEQUENCE: 4
atggacacta agatcggatc tatcgacgcg tgtaacccga ccaaccacga tatcggcggt       60
cctccaaacg gcggagtctc caccgttcaa aacacaagtc cacttcactc caccaccgtc      120
agccctgcg acgcgactct tggccgttac ctagcaagac ggttagtcga atcggcgtc        180
accgatgtct ctccgttcc tggtgatttc aacctgacgc ttctcgatca cctaatcgcc       240
gaaccaaacc tcaagctgat cggttgctgc aacgagctta cgccggata cgctgctgac      300
ggttacgcta gatctcgcgg tgttggtgcg tcgtcgtta cgttcaccgt cggtggattg       360
agtgttctga atgcgatcgc cggtgcttac agtgagaatc tgcctctgat ttgcatcgtc      420
ggtggtccaa actccaacga ttacggtacc aataggattc ttcatcatac aattggttta     480
cctgatttca ctcaagagct taggtgtttt caagctgtta cttgttttca agctgtgatt     540
aataacttag aagaggctca tgaacttatc gatactgcga tttcaactgc tttgaaagaa     600
agcaaacctg tttatatcag tatcagctgt aatttaccgg cgattcctct tccgacgttt     660
agtcgtcatc ctgttccgtt catgcttccg atgaaggtta gcaatcagat tggtttagat    720
gcggcggtgg aggcagctgc tgagttcttg aacaaagctg tgaagccagt tcttgttggt     780
gggccgaaaa tgcgggttgc gaaagccgcg gatgcttttg ttgagcttgc tgatgcttct     840
ggctatggtc ttgctgtgat gccttctgct aaaggacaag tacctgagca tcacaagcat     900
tttataggga cgtattgggg agctgtgagt acagcttttt gtgctgaaat cgttgaatct     960
gcggatgctt atctgtttgc aggtccgatt ttcaacgatt acagttctgt tgggtattct   1020
```

```
ctgcttctca agaaggagaa ggcaatcatc gttcagcctg atcgggttac tatcggtaac    1080
ggacctgcgt ttggatgtgt tcttatgaag gattttctaa gcgagttggc taaacgaatt    1140
aagcacaaca acacttctta tgagaattat cacaggatct atgtcccaga aggaaagcct    1200
ttgagagata acccgaatga gtctttgagg gttaatgtac tgttccaaca cattcagaat    1260
atgctctctt ctgagtctgc tgtgcttgct gagacaggag attcctggtt caactgtcag    1320
aagctgaagc tccctgaagg atgcggttac gaattccaaa tgcagtacgg atcaattggc    1380
tggtcagtgg gtgctactct aggctatgct caagccatgc caaacaggcg tgtcattgct    1440
tgtattggag atggtagttt ccaggtaacc gcacaggatg tatctacgat gatacggtgt    1500
gggcaaaaga ccataatctt cctcatcaac aacggaggct acaccattga ggtggaaatt    1560
cacgatggtc cttacaatgt cataaagaac tggaactaca cagcttttgt tgaggccata    1620
cacaatggag aaggaaaatg ctggactgcc aaggtgagat gcgaggagga gttagtgaaa    1680
gcaatcaaca cggcaaccaa tgaggaaaaa gagagctttt gtttcattga agtgatagtg    1740
cacaaagacg atacaagcaa ggaacttttg gagtggggct ctagagtctc tgctgctaat    1800
agtcgtcccc caaatccgca gtag                                          1824

<210> SEQ ID NO 5
<211> LENGTH: 1824
<212> TYPE: DNA
<213> ORGANISM: Arabidopsis thaliana

<400> SEQUENCE: 5
atggacacca aaatcggatc gatcgatgat tgcaagccga cgaacggcga cgtctgtagt      60
ccaacaaacg gcaccgtcgc aacaatccac aactctgttc cttcctccgc tatcaccatc     120
aactactgcg acgcgactct cggccgtcac ttagctcgtc gtctcgtcca agccggcgtt     180
acggatgttt tctctgttcc cggagatttc aacctcactt tgcttgatca cctcatggct     240
gagccggacc tcaacctaat cggatgttgt aacgagctaa cgccggtta cgctgccgac     300 ggttacgcta gatctcgtgg agtcggcgct tgcgttgtta ccttcaccgt tggtggactc     360
agcgttttaa acgcgatcgc tggtgcttac agcgagaatc ttcctcttat ctgtatcgtc     420
ggaggtccta actctaacga ttatggcact aaccggattc ttcatcacac cattggatta     480
cctgatttta gccaagagct taggtgcttc caaacggtga cttgttatca ggcggtggtg     540
aacaatttag atgatgctca tgaacagatt gataaagcaa tatcaacagc tttgaaagag     600
agcaagcctg tgtatataag tgtaagctgt aacttagcag cgattcctca tcatacattt     660
agccgtgatc ctgtcccttt ttctctagct ccaagattga gcaacaagat gggtttagaa     720
gctgcggtgg aagcaacatt ggagtttctg aataaggctg tgaagccagt tatggttggt     780
ggtcctaagt tgcgtgtggc taaagcttgt gatgcctttg ttgagctagc tgatgcttca     840
ggctatgctt tggcgatgat gccttctgcg aaaggctttg taccagagca ccatcctcat     900
ttcattggaa cttattgggg agcagtgagc actccttttt gctctgagat tgtggaatct     960
gcggatgctt acatttttgc aggtccaatc ttcaacgact atagctctgt tggttactcg    1020
cttctcctca gaaagaaaaa agccatcgtt gtgcaacctg atcgtatcac tgtggccaat    1080
ggtcctactt ttggttgcat tttgatgagc gatttcttca gggaattgtc taagagggtg    1140
aagcgtaacg agactgcata tgagaactac cataggatct tgtccctga aggtaagcca    1200 ttgaagtgtg aatcaagaga gccattgaga gttaacacaa tgttccagca cattcagaag    1260
```

```
atgctctcta gtgaaaccgc tgtgattgct gaaaccggtg attcttggtt caattgccaa   1320
aaactaaagc tgccaaaagg atgtgggtac gagtttcaga tgcagtatgg atcgattggg   1380
tggtctgttg gtgcaactct aggatacgca caggcatcac cagagaagcg agtgttggca   1440
ttcatcggtg atgggagttt ccaagtcacg gttcaggaca tatcaacaat gctgcgtaat   1500
ggacagaaga cgatcatctt cttgattaac aatggtggct acaccattga agtagagatt   1560
catgacggtc cttataacgt gattaagaac tggaactaca ctggtctcgt tgacgccatt   1620
cataacggtg aaggcaattg ctggactgca aaggtgagat acgaagagga gttagtggag   1680
gcgattacga cagcgacgac ggagaagaaa gattgtctat gtttcataga agtgattctt   1740
cacaaggatg atacgagcaa agagttgctt gagtggggct cacgcgtctc tgctgctaac   1800
agccgtcctc ccaatcctca gtag                                          1824

<210> SEQ ID NO 6
<211> LENGTH: 1695
<212> TYPE: DNA
<213> ORGANISM: Saccharomyces kluyveri

<400> SEQUENCE: 6
atgtccgaaa ttactctagg tctctacttg tttgaaagac tgaaccaagt cgatgttaaa     60
accattttcg gtttgccagg tgactttaac ttgtccttgt tggacaagat ctacgaagtc    120
ccaggtatga gatgggctgg taacgctaac gaattgaacg ctgcttacgc tgctgacggt    180
tacgctagag ttaagggtat gtcctgtatc atcaccacct tcggtgtcgg tgaattgtct    240
gccttgaacg gtattgccgg ttcttatgct gaacacgttg gtgttttgca cgttgtcggt    300
gttccatccg tctcttccca agctaagcaa ttgttgttgc atcacacctt gggtaacggt    360
gacttcactg tcttccacag aatgtctgcc aacatctctg aaaccaccgc ttgggttacc    420
gacattgcca ctgccccagc tgaaattgac agatgcatca gaaccaccta cgtcacccaa    480
agaccagtct acttgggttt gccagccaac ttggttgact tgatggtccc agcttctttg    540
ttggacaccc caattgactt gtctctaaag ccaaacgacc cagaagccga agctgaagtt    600
gtcaacagcg tcttggaatt gatcaaggac gctaagaacc caattatctt ggccgatgcc    660
tgtgcttcca cacgacgt caagcctgaa actaagcaat tgatcgacat tacccaattc    720
ccagccttcg ttacccccatt gggtaagggt tccatcgacg aacaacaccc aagattcggt    780
ggtgtttacg tcggtacctt gtctaacgac gatgtcaagg aagccgttga atctgctgac    840
ttgattctat ctgtcggtgc tttgttgtcc gacttcaaca ccggttcttt ctcttactct    900
tacaagacca gaacattgt tgaattccac tctgactaca tcaagatcag aaacgctacc    960
ttcccaggtg tccaaatgaa atttgcattg caaaagttgt tgtctgaaat cggtgcagtt   1020
gttaaggact acaagccagt tgctgttcca ccaaagccaa ctccaaaccc agcttgtgac   1080
ccatccaccc cattgaagca agaatgggtc tggaaccaag tcggtagatt cttgcaagaa   1140
ggtgacgttg tcatcactga aaccggtacc tccgctttcg gtatcaacca aactcatttc   1200
cctaacaata cttacggtat ctcccaagtc ttatggggtt ctatcggttt caccaccggt   1260
gcttgtttgg gtgctgcttg cgctgctgaa gaacttgaca agaacaagag agtcatccta   1320
ttcattggtg acggttcttt gcaattgact gttcaagaaa tctccaccat gatcagatgg   1380
ggtctaagac catacttgtt cgtcttgaac aacgacggtt acaccattga aagattgatt   1440
cacggtgaaa acgctcaata caacgaaatt caaccatgga gaacttgga cctattgcca   1500 accttcggtg ctaaggacta cgaaacctac agagtcgcca ctaccggtga atgggacaag   1560
```

```
ttggcccaag acgaggcctt caacaagaac tccagaatca gaatggttga agttatgcta    1620
cctgttatgg atgctccatc taacttggtc aagcaagccc aattgactgc tagcatcaac    1680
gccaagcaag attaa                                                     1695

<210> SEQ ID NO 7
<211> LENGTH: 1733
<212> TYPE: DNA
<213> ORGANISM: Candida glabrata

<400> SEQUENCE: 7
atgtctgaaa ttactttggg tagatacttg ttcgagagat tgaaccaagt cgacgttaag      60
accatcttcg gtttgccagg tgacttcaac ttgtccctat tggacaagat ctacgaagtt     120
gaaggtatga gatgggctgg taacgctaac gaattgaacg ctgcttacgc tgctgacggt     180
tacgctagaa tcaagggtat gtcctgtatc atcaccacct tcggtgtcgg tgaattgtct     240
gccttgaacg gtattgccgg ttcttacgct gaacacgtcg gtgtcttgca cgtcgtcggt     300
gtcccatcca tctcctctca agctaagcaa ttgttgttgc accacacctt gggtaacggt     360
gacttcactg tcttccacag aatgtccgct aacatctctg agaccaccgc tatggtcact     420
gacatcgcta ccgctccagc tgagatcgac agatgtatca gaaccaccta catcacccaa     480
agaccagtct acttgggtct accagctaac ttggtcgacc taaaggtccc agccaagctt     540
ttggaaaccc caattgactt gtccttgaag ccaaacgacc cagaagccga actgaagtc     600 gttgacaccg tcttggaatt gatcaaggct gctaagaacc cagttatctt ggctgatgct     660
tgtgcttcca gacacgacgt caaggctgaa accaagaagt tgattgacgc cactcaattc     720
ccatccttcg ttaccccaat gggtaagggt tccatcgacg aacaacaccc aagattcggt     780
ggtgtctacg tcggtacctt gtccagacca gaagttaagg aagctgttga atccgctgac     840
ttgatcttgt ctgtcggtgc tttgttgtcc gatttcaaca ctggttcttt ctcttactct     900
tacaagacca gaacatcgt cgaattccac tctgactaca tcaagatcag aaacgctacc     960
ttcccaggtg tccaaatgaa gttcgctttg caaaagttgt tgaacgccgt cccagaagct    1020
atcaagggtt acaagccagt ccctgtccca gctagagtcc agaaaacaa gtcctgtgac    1080 ccagctaccc cattgaagca agaatggatg tggaaccaag tttccaagtt cttgcaagaa    1140
ggtgatgttg ttatcactga aaccggtacc tccgcttttg gtatcaacca acccccattc    1200
ccaaacaacg cttacggtat ctcccaagtt ctatggggtt ccatcggttt caccaccggt    1260
gcttgtttgg gtgccgcttt cgctgctgaa gaaatcgacc caagaagag agttatcttg    1320 ttcattggtg acggttcttt gcaattgact gtccaagaaa tctccaccat gatcagatgg    1380
ggcttgaagc catacttgtt cgtcttgaac aacgacggtt acaccatcga aagattgatt    1440
cacggtgaaa aggctggtta caacgacatc caaaactggg accacttggc tctattgcca    1500
accttcggtg ctaaggacta cgaaaaccac agagtcgcca ccaccggtga atgggacaag    1560
ttgacccaag acaaggaatt caacaagaac tccagatca gaatgatcga agttatgttg    1620
ccagttatgg acgctccaac ttccttgatt gaacaagcta agttgaccgc ttccaccaac    1680
gctaagcaat aagttgaccg cttccaccaa cgctaagcaa taagctcgag aac           1733
```